(12) United States Patent
Lounsberry et al.

(10) Patent No.: US 6,412,980 B1
(45) Date of Patent: *Jul. 2, 2002

(54) METHOD AND APPARATUS FOR CONFIGURING AND MONITORING A SYSTEM UNIT IN A MEDICAL DIAGNOSTIC SYSTEM

(75) Inventors: Brian D. Lounsberry, Thiensville; Jonathan R. Schmidt, Wales; Stephen W. Gravelle; Michael S. Idelchik, both of Mequon, all of WI (US); James S. Shepard, Montclair, NJ (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,713

(22) Filed: Dec. 30, 1999

(51) Int. Cl.[7] .................................................. H05G 1/54
(52) U.S. Cl. ....................................... 378/207; 378/114
(58) Field of Search ................................ 378/108, 110, 378/112, 114, 117, 118, 207

(56) References Cited

U.S. PATENT DOCUMENTS 4,991,193 A * 2/1991 Cecil et al. .................. 378/117
5,434,900 A * 7/1995 Tanaka et al. ................. 378/15
6,212,256 B1 * 4/2001 Miesbauer et al. ......... 378/118
6,325,540 B1 * 12/2001 Lounsberry et al. ........ 378/114

* cited by examiner

Primary Examiner—David P. Porta
(74) Attorney, Agent, or Firm—Foley & Lardner; Peter J. Vogel; Michael A. Della Penna

(57) ABSTRACT

A method for configuring and monitoring a system unit in a medical diagnostic system includes establishing a communication connection between the medical diagnostic system and a remote facility, communicating characteristic information regarding operation of the system unit in the medical diagnostic system from the remote facility to the medical diagnostic system, configuring the medical diagnostic system in accordance with the characteristic information regarding operation of the system unit, and monitoring the operation information of the system unit in the medical diagnostic system using an operator workstation at the medical diagnostic system. A corresponding apparatus includes a storage medium coupled to the system unit which stores information for the system unit in the medical diagnostic system and a communication interface configured to allow communications between the medical diagnostic system and a remote facility. The communications provide for the configuring of the medical diagnostic system to accept the system unit and for monitoring of the system unit.

25 Claims, 7 Drawing Sheets

METHOD AND APPARATUS FOR CONFIGURING AND MONITORING A SYSTEM UNIT IN A MEDICAL DIAGNOSTIC SYSTEM

BACKGROUND OF THE INVENTION

The present invention relates generally to the field of medical diagnostic systems, such as imaging systems. More particularly, the present invention relates to a technique for configuring and monitoring a system unit in a medical diagnostic system. Configuration and monitoring a system unit includes providing field service, upgrades, characterization data, and so forth to imaging systems. Further, configuration and monitoring a system unit provides for automatic configuration of the system to the particular field replaceable unit.

One such field replaceable unit is an x-ray tube. X-ray tubes are used in a variety of imaging systems, such as, for example, CT systems. Other field replaceable units may be included in vascular imaging systems, R&F (radiography and fluoroscopy) systems, mammography systems, and the high voltage (HV) x-ray generators of these systems. X-ray tubes are passive components on imaging systems that require external power supplies (e.g., HV generator, motor controller, filament supply) for their operation. X-ray tubes also need characterization data for the control of their operation (e.g., x-ray tube cooling algorithms and data for software control of exposure). The association of the tube with a particular x-ray system/generator involves providing characterization information to the system/generator operating system and/or component operating systems. Proper association of the tube permits the tube to be operated correctly.

Conventional systems generally achieve the association of a tube with a particular x-ray system/generator in one of two ways. In one conventional method, the information about a given model x-ray tube is "hard coded" into the operating system software so that the system will operate all tubes in the same manner, regardless of the tube's actual characteristics. In a second conventional method, a set of pre-known tube characteristics are coded into the system/generator operating system and provision is made for selection of the appropriate set of operating characteristics of a limited number of different tube models for that given system.

The first conventional method does not provide for any positive identification that the x-ray tube being operated is the one for which the system has been configured, nor is there a way to change the configuration for a different tube model. The second conventional method usually involves some rudimentary model identification method. For example, a human operator reads model plate information and enters the information into a system configuration table. Alternatively, some parameter is sensed by the system. In the second conventional method, some limited number of tubes with different operating characteristics can be associated, but this information must be known at the time of the original system configuration. Any new information for new model tubes or upgrades of current model tubes must be coded into a new release of the system software and must be loaded onto the system/generator.

The passive nature of the x-ray tube as a component also comes into play when the tube is replaced for failure in a system operating in the field. Important data characterizing the tube's operation leading up to and at the time of failure is only available at the system level. A tube returned to the factory carries no such data except for possibly written data from a service person. However, such information is often limited and occasionally omitted when the tube is removed by the service person.

Conventional methods of associating x-ray tubes (or any other field replaceable unit) with the system do not provide for the association of new tube designs. If a new tube design is introduced, the system may need to be re-coded and the operating system re-released. Further, conventional methods do not allow for product tiers around a given model tube. For example, a system cannot use a higher performance level tube without re-coding and re-releasing system operating software, including expensive and time consuming Field Modification Instructions (FMI's). New characteristics for a particular tube may be established as new information becomes available on the operation of that tube model. FMI's to reconfigure a system to different tube characteristics typically involve a technician visit and down-time (i.e., non-operational time) for the system.

Thus, there is a need for a method and apparatus to provide for the association of field replaceable units, such as x-ray tubes, with medical diagnostic systems. Further, there is a need for a method and apparatus to provide for the association of field replaceable unit designs. Further, there is a need for a method and apparatus to operate a given model unit under different operating conditions. Even further, there is a need for a method and apparatus to query and positively identify the unit model of a given unit in a given field system and/or change the operating characteristics of that unit while it is installed. Even still further, there is a need for a method and apparatus to get consistent and accurate field usage data back on a unit upon return to the factory. Such data is valuable in making critical business decisions.

BRIEF SUMMARY OF THE INVENTION

One embodiment of the invention relates to a method for configuring and monitoring a system unit in a medical diagnostic system. The method includes establishing a communication connection between the medical diagnostic system and a remote facility, communicating characteristic information regarding operation of the system unit in the medical diagnostic system from the remote facility to the medical diagnostic system, configuring the medical diagnostic system in accordance with the characteristic information regarding operation of the system unit, and monitoring the operation information of the system unit in the medical diagnostic system using an operator workstation at the medical diagnostic system.

Another embodiment of the invention relates to an apparatus which provides for the configuring and monitoring of a system unit in a medical diagnostic system. The apparatus includes a storage medium coupled to the system unit which stores information for the system unit in the medical diagnostic system and a communication interface configured to allow communications between the medical diagnostic system and a remote facility. The communications provide for the configuring of the medical diagnostic system to accept the system unit and for monitoring of the system unit.

Another embodiment of the invention relates to a system for configuring and monitoring a system unit in the medical diagnostic system. The system includes means for communicating characteristic information regarding operation of the system unit in the medical diagnostic system from the remote facility to the medical diagnostic system, means for configuring the medical diagnostic system in accordance with the characteristic information from the remote facility, means for communicating operation information of the system unit in the medical diagnostic system to the remote facility, and means for monitoring the operation information of the system unit in the medical diagnostic system.

Other principle features and advantages of the present invention will become apparent to those skilled in the art upon review of the following drawings, the detailed description, and the appended claims.

BRIEF DESCRIPTION OF THE DRAWINGS

The invention will become more fully understood from the following detailed description, taken in conjunction with the accompanying drawings, wherein like reference numerals denote like elements, in which.

DETAILED DESCRIPTION OF THE INVENTION

Figure 1:
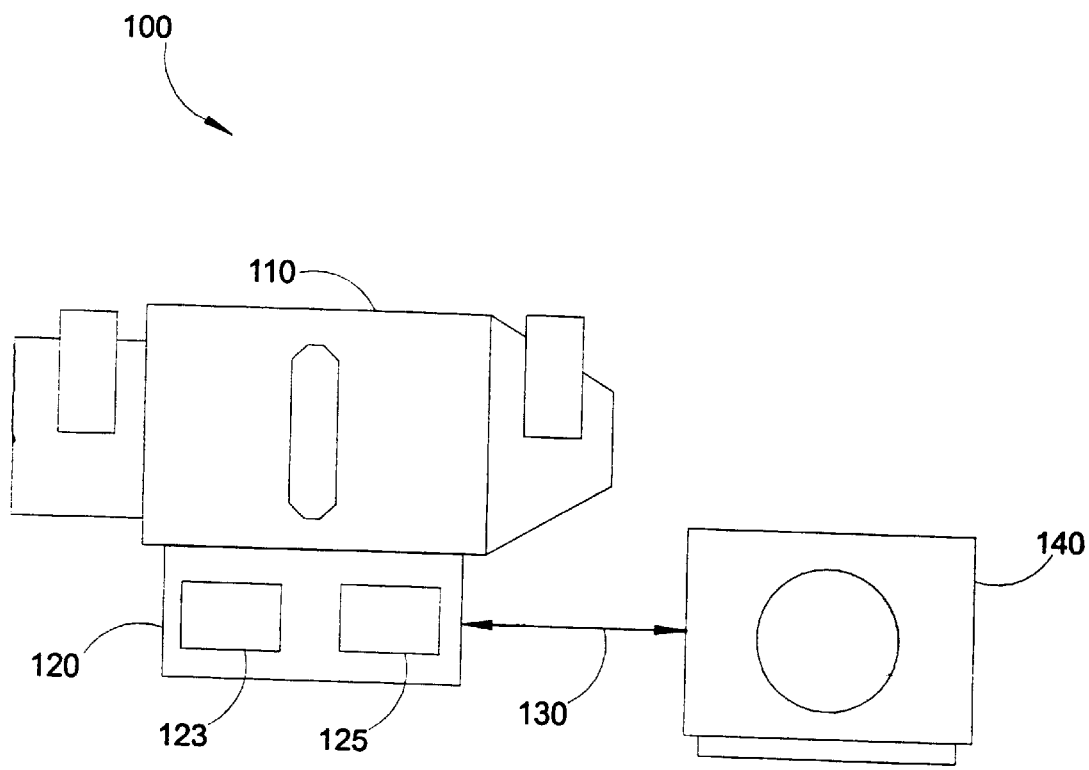
FIG. 1 is a diagrammatical representation of an x-ray imaging system including a preferred embodiment of the present invention.

FIG. 1 is a general block diagram of a x-ray imaging system 100. System 100 includes an x-ray tube unit 110, an electronic device 120, a data communication link 130, and an imaging unit 140. In an alternative embodiment, imaging system 100 is any of a variety of imaging systems (e.g., CT systems, vascular imaging systems, R&F (radiography & fluoroscopy) systems, mammography systems, high voltage x-ray generators). Such alternative embodiments include components characteristic to the particular type of imaging system used. Indeed, x-ray tube unit 110 can be any of a variety of field replaceable units or system units associated with a medical imaging system.

X-ray tube unit 110 generates x-rays which pass through a body of interest (e.g., part of the human body). Preferably, electronic device 120 comprises a storage medium 123 and a programmed digital processing circuit or, in the present instance, a microcontroller 125. Storage medium 123 is any of a variety of memory components which allow for the reading and writing of non-volatile data, such as, battery-backed RAM (random access memory), EPROM (electrically programmable read only memory) and EEPROM (electrically-erasable programmable read only memory). Preferably, storage medium 123 includes a readable/writeable memory module having a first memory portion which is read-only and a second memory portion which is readable and writeable. Microcontroller 125 is coupled to storage medium 123 and is responsive to requests for identification information from operating system 140 via data communication link 130. Alternatively, electronic device 120 comprises only storage medium 123. Data communication link 130 couples electronic device 120 to imaging unit 140 for communication of data between electronic device 120 and imaging unit 140. Data communication link 130 is a serial interface, a RS232 line, or any other communication connection. In an exemplary embodiment, electronic device 120 is physically attached to x-ray tube unit 110.

Electronic device 120 contains information both generic and specific to x-ray tube unit 110. Such information can include operating model identification information, such as model number, serial number, and manufacturing date, as well as x-ray tube unit operating characteristics, such as, tube cooling algorithm coefficients and limits, filament characteristics, motor characteristics, and off-focal radiation kernels. X-ray tube unit information is preferably contained as read-only data sets in storage medium 123 of electronic device 120. Alternatively, the information is encoded into storage medium 123 of electronic device 120. Some of the data contained within electronic device 120 may be common to the particular tube type (e.g., model number, tube cooling algorithm coefficients), some of the data may be selectable (e.g., tube cooling algorithm limits), and some of the data may be specific to the individual tube (e.g., the filament calibration data, serial number, manufacturing date).

When x-ray tube unit 110 is installed into imaging system 100, electronic device 120 is connected through data communication link 130 for access by imaging unit 140. Imaging unit 140 includes an operating system which coordinates and directs the operations of imaging system 100. The operating system is preferably configured to require the download of x-ray tube unit identification information and operating characteristics into system memory in order for imaging system 100 to operate. The operating system automatically configures imaging unit 140 and imaging system 100 to correct and optimal operational settings based on the operating characteristics it receives.

During operation of imaging system 100, certain system-available pieces of information are sent to the writeable memory of electronic device 120 regarding the operation of x-ray tube unit 110. Electronic device 120 is preferably physically coupled to x-ray tube unit 110. As such, system information resides with x-ray tube unit 110 as it is returned to the factory or tube loading facility for autopsy and disposal. Examples of system-available pieces of information sent to electronic device 120 include system usage counter information, rotor on time, error log information, site installation information, and technique usage information.

Figure 2:
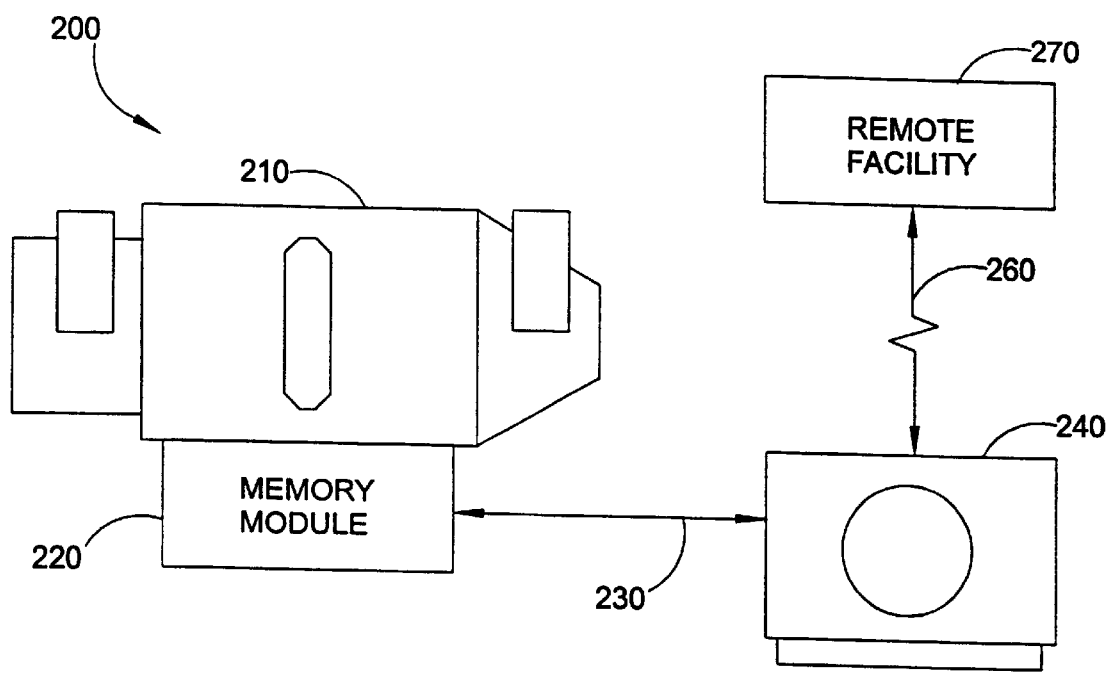
FIG. 2 is a diagrammatical representation of an alternative embodiment of the x-ray imaging system of FIG. 1.

Referring now to FIG. 2, an x-ray imaging system 200 is shown. System 200 includes an x-ray tube unit 210, a memory module 220, a data communication link 230, an imaging unit 240, a telecommunication link 260, and a remote facility 270. System 200 is similar to system 100 with the exceptions that memory module 220 is an on-board memory device storing identification information, a programmed digital processing circuit or microcontroller is contained within imaging unit 240, and system 200 is capable of remote communications via telecommunications link 260. Memory module 220 is physically coupled to x-ray tube unit 210. Alternatively, memory module 220 is an electronic device, such as electronic device 120, which is also physically coupled to x-ray tube unit 210.

In a remote communication mode, x-ray tube unit characterization data such as tube cooling algorithm coefficients and limits, and motor characteristics are downloaded to the operating system of imaging unit 240 via telecommunication link 260 from remote facility 270. The characterization data is then downloaded from remote facility 270 to imaging unit 240 via telecommunication link 260. Identification (ID) information is required in order to download the information from remote facility 270. Such ID information determines what possible operating characteristics are downloaded. The range of operating characteristics depends on, for example, level of service, product tier, etc. ID information is used at remote facility 270 for authentication with a subscription file, as described in detail below.

Recording of system operating and failure history to memory module 220 operates in a similar manner, as described with respect to x-ray imaging system 100, except that information can be communicated (i.e., uploaded) to remote facility 270 via telecommunications link 260. As such, servicing decisions or autopsy analysis may be done remotely. Preferably, however, failure history is recorded in memory module 220 such that the information is available during autopsy analysis of x-ray tube unit 210 when removed from the system.

Figure 3:
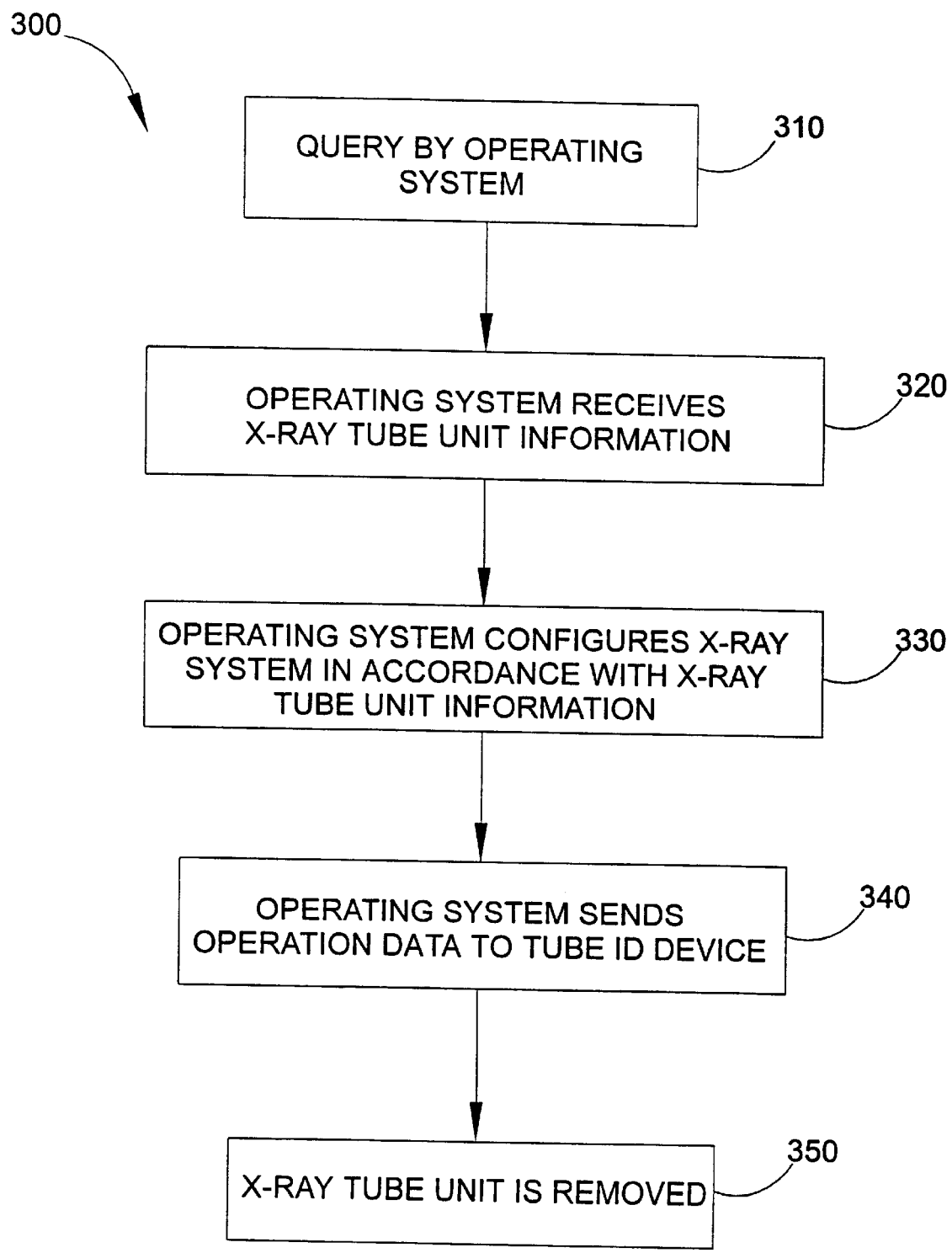
FIG. 3 is a flowchart of example operations of the x-ray imaging system of FIG. 1.

Referring now to FIG. 3, a flowchart 300 illustrates the general operation of x-ray imaging system 100 or 200. In a step 310, the operating system of the imaging unit queries for field replaceable unit or system unit information. After step 310, a step 320 is performed in which the operating system receives information regarding x-ray tube unit 110 or 210. In the exemplary system shown in FIG. 1 (system 100), identification and characterization information are preferably provided by electronic device 120. In the exemplary imaging system shown in FIG. 2 (system 200), identification information is preferably provided by memory module 220 and characterization information is provided by remote facility 270. Identification and characterization information can be device generic or specific. For example, generic information may include a model number, cooling algorithm coefficients and limits, motor/filament characteristics, and off-focal radiation kernals. Specific information may include serial number, manufacturing date, and filament calibration data.

After step 320, a step 330 is performed in which the operating system configures the x-ray imaging system in accordance with x-ray tube unit information received. After step 330, a step 340 is performed in which the operating system sends data regarding the operation of the x-ray imaging system to electronic device 120 in the case of imaging system 100 or remote facility 270 in the case of imaging system 200. Step 340 continues periodically throughout the life of the x-ray tube unit or at the end of the x-ray tube unit life until the x-ray tube unit is removed.

Figure 4:
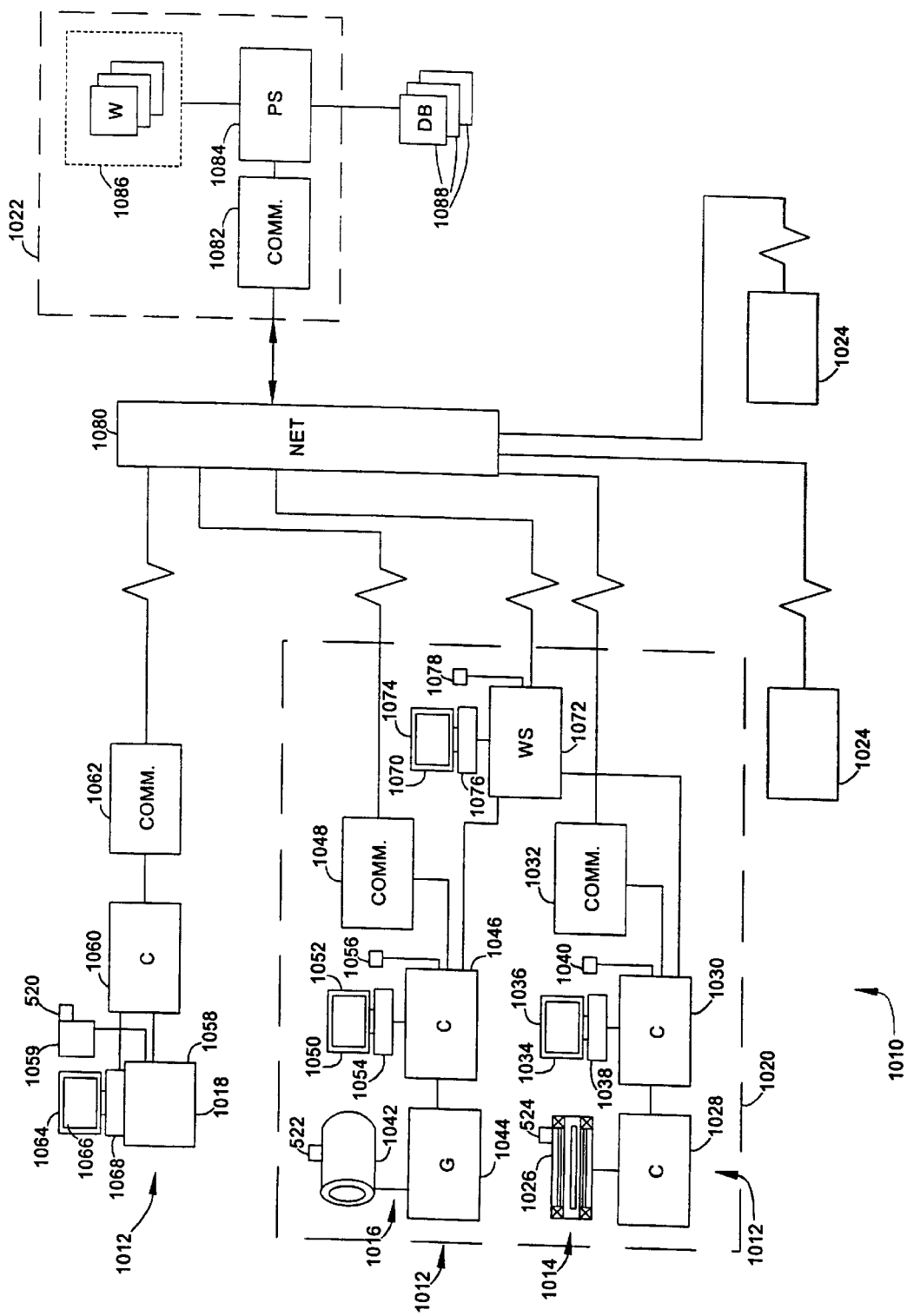
FIG. 4 is a diagrammatical representation of a series of medical diagnostic systems coupled to a remote facility via a network connection for providing remote services and data interchange between the diagnostic systems and the remote facility.

Referring now to FIG. 4, a service system 1010 is illustrated for providing remote services to a plurality of medical diagnostic systems 1012. Medical diagnostic systems 1012 can include a variety of medical diagnostic systems, such as, x-ray imaging system 200 described with reference to FIG. 2. In particular, service system 1010 provides for remote configuration of medical diagnostic systems 1012, remote maintenance or servicing, and remote monitoring of system operation.

Remote configuration, maintenance, and monitoring are specifically applicable where field replaceable units are used, but such remote services apply equally to systems containing field replaceable units and systems containing non-replaceable units. Furthermore, service system 1010 also provides for other remote services, such as, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. Moreover, the various modality systems serviced in accordance with the present techniques may be of different type, manufacture, and model.

In the embodiment illustrated in FIG. 4, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

Depending upon the modality of the systems, various subcomponents or subsystems will be included. For example, MRI system 1014 generally includes a scanner 1026, a control and signal detection circuit 1028, a system controller 1030, a communication module 1032, and operator station 1034. CT system 1016 generally includes a scanner 1042, a generator and controller 1044, a system controller 1046, a communications module 1048, and an operator station 1050. Ultrasound system 1018 typically includes a scanner and data processing unit 1058, an ultrasound probe 1059, a system controller 1060, a communications module 1062 and an operators station 1064.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment benefiting from the present techniques may include imaging systems, clinical diagnostic systems, physiological monitoring systems and so forth.

In the case of MRI system 1014, scanner 1026 generates pulsed magnetic fields and collects signals from emissions by gyromagnetic material within a subject of interest. The scanner is coupled to control and signal detection circuit 1028 which, in turn, is coupled to system controller 1030. System controller 1030 includes a uniform platform for interactively exchanging service requests, messages and data with service facility 1022 as described more fully below. System controller 1030 is linked to communications module 1032, which may be included in a single or separate physical package from system controller 1030. System controller 1030 is also linked to operator station 1034 which will typically include a computer monitor 1036, a keyboard 1038, as well as other input devices 1040, such as a mouse.

In the case of CT system 1016, scanner 1042 detects portions of x-ray radiation directed through a subject of interest. Scanner 1042 is coupled to generator and controller, as well as to a signal acquisition unit, represented collectively at reference numeral 1044, for controlling operation of an x-ray source and gantry within scanner 1042, and for receiving signals produced by a detector array moveable within the scanner. The circuitry within the controller and signal acquisition components is coupled to system controller 1046 which includes circuitry for commanding operation of the scanner and for processing and reconstructing image data based upon the acquired signals. System controller 1046 is linked to communications module 1048 for transmitting and receiving data for remote services. Also, system controller 1046 is coupled to operator station 1050 which includes a computer monitor 1052, a keyboard 1054, as well as other input devices 1056, such as a mouse.

In the case of ultrasound system 1018, scanner and data processing unit 1058 transmits ultrasound signals into a subject of interest, and acquires resultant signals which are processed for reconstructing a useful image. System controller 1060 regulates operation of scanner and data processing unit 1058 and processes acquired signals to reconstruct the image. Moreover, communications module 1062 transmits service requests, messages and data between system controller 1060 and service facility 1022. Operators station 1064 includes a monitor 1066, as well as input devices such as a keyboard 1068. Additional components may be included in systems 1014, 1016, and 1018, such as a printer or photographic system for producing reconstructed images based upon data collected from scanner 1026.

Where more than one medical diagnostic system is provided in a ingle facility or location 1020, as indicated in the case of MRI and CT systems 1014 and 1016 in FIG. 4, these may be coupled to a management station 1070, such as in a radiology department of a hospital or clinic. The management station may be linked directly to controllers for the various diagnostic systems, such as controllers 1030 and 1046 in the illustrated embodiment. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless may be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 4. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment. As described below, such databases may be employed both for servicing of particular diagnostic systems and for tracking such servicing, as well as for deriving comparison data for use in servicing a particular system or a family of systems.

Service system 1010 specifically provides automatic configuration, maintenance, and monitoring using electronic devices 520, 522, and 524. Electronic device 520 is coupled to ultrasound probe 1059 and includes information relating to ultrasound probe 1059. Such information can include identification information and/or operational information. Electronic device 520 provides for the automatic configuration and/or monitoring of ultrasound system 1018 to the particular ultrasound probe 1059 used. Automatic configuration and/or monitoring of ultrasound system 1018 can be accomplished directly using electronic device 520. Alternatively, automatic configuration, maintenance, and/or monitoring of ultrasound system 1018 can be accomplished via remote facility 1022.

Advantageously, electronic device 520 provides positive identification of ultrasound probe 1059. As such, ultrasound system 1018 can be protected from either improper installation of a probe or an attempt to install and operate a probe which was not properly characterized for operation on ultrasound system 1018. Further, electronic device 520 coupled to ultrasound probe 1059 allows for easy, fast, and low cost introductions of new probe operations. As such, new probes or probe upgrades can be utilized immediately from the factory without service intervention or field modification instructions (FMI's ). Further, usage information and operational data from ultrasound system 1018 can be provided to remote facility 1022 for a variety of uses.

Electronic device 522 is coupled to the x-ray source contained in scanner 1042 of CT system 1016 and includes information relating to the x-ray source. Such information can include identification information and/or operational information. Electronic device 522 provides for the automatic configuration and/or monitoring of CT system 1016 to the particular x-ray source used. Automatic configuration and/or monitoring of CT system 1016 can be accomplished directly, as is done with electronic device 120 in imaging system 100 described with reference to FIG. 1. Alternatively, automatic configuration, maintenance, and/or monitoring of CT system 1016 can be accomplished via remote facility 1022, as is done with memory module 220 in imaging system 200 described with reference to FIG. 2.

Advantageously, positive identification of a tube model used as the x-ray source in CT system 1016 protects the system from either improper installation of an x-ray tube or an attempt to install and operate a tube which was not properly characterized for operation on the imaging system in question. Further, electronic device 522 allows for easy, fast, and low cost introductions of new tube offerings to the field through factory or remote programmable characteristics. As such, new tubes can be utilized immediately from the factory without service intervention or field modification instructions (FMI's). Electronic device 522 further allows for easy functional and performance differentiation of a single tube model for tiered offerings.

Electronic device 522 using remote capabilities, as described in detail with reference to x-ray imaging system 200 and FIG. 2, provides for the switching of performance levels on a given tube at any point (e.g., in the middle) of its operating life. As such, CT system 1016 with electronic device 522 using remote capabilities avoids having to pull tubes from stock and reprogram them in the case of a programming error or the addition of a previously unprogrammed characterization.

Electronic device 524 is coupled to scanner 1026 of MRI system 1014 and includes information relating to scanner 1026. Electronic device 524 provides for the automatic configuration and/or monitoring of MRI system 1014 to the particular scanner 1026 used. Automatic configuration, maintenance, and/or monitoring of MRI system 1014 can be accomplished directly or via remote facility 1022.

Advantageously, a variety of system components on MRI system 1014 can be monitored and configured for use with the system. Electronic device 524 provides system components such as scanner 1026 with a "black box" which records operational data for determinations of causes for component events, such as failure. Further, electronic device 524 provides for identification of MRI system 1014 for other services available from remote facility 1022.

Figure 5:
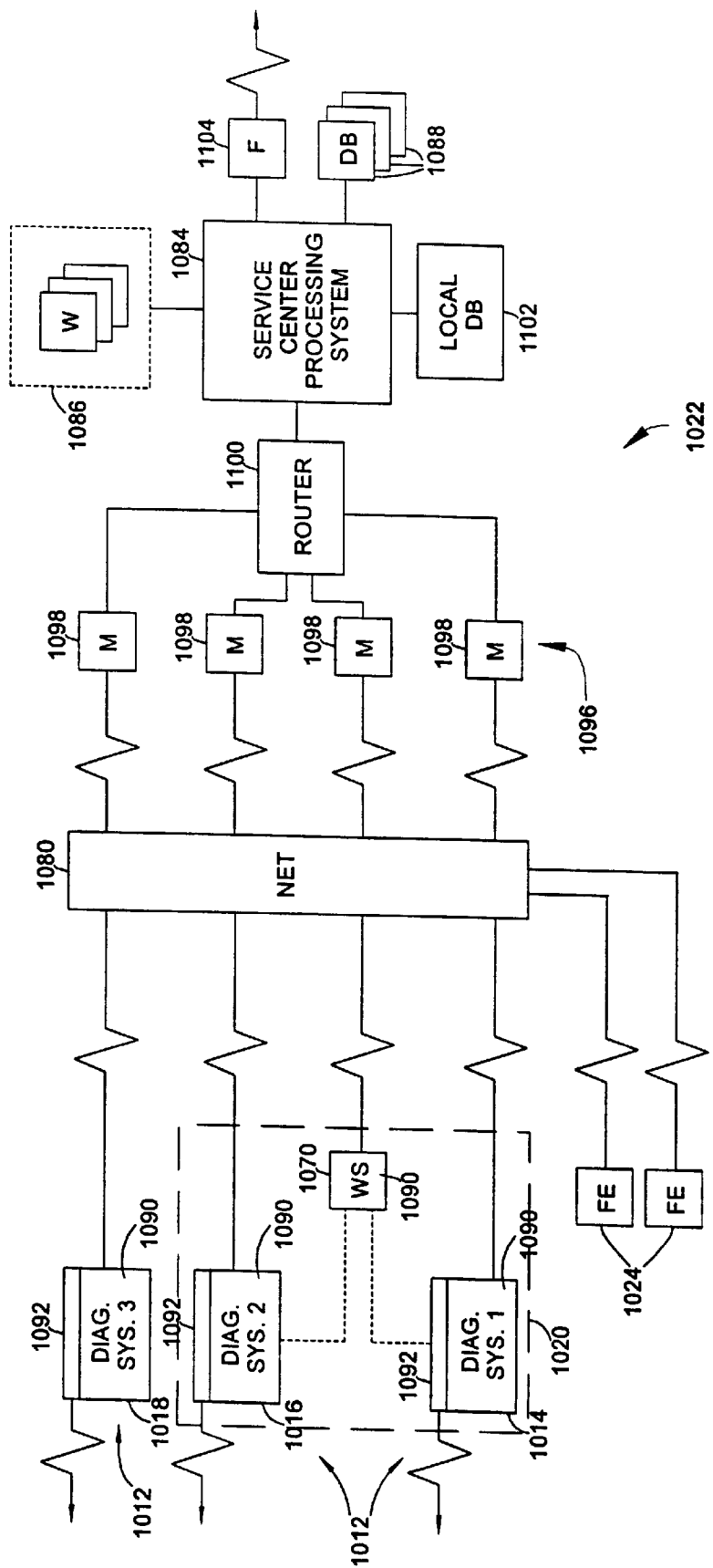
FIG. 5 is a block diagram of the systems shown in FIG. 4, illustrating certain functional components of the diagnostic systems and the remote facility.

FIG. 5 is a block diagram illustrating the foregoing system components in a functional view. As shown in FIG. 5, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 6, includes hardware, firmware, and software components adapted for transmitting and receiving data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for remote functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the remote facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 5, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 6:
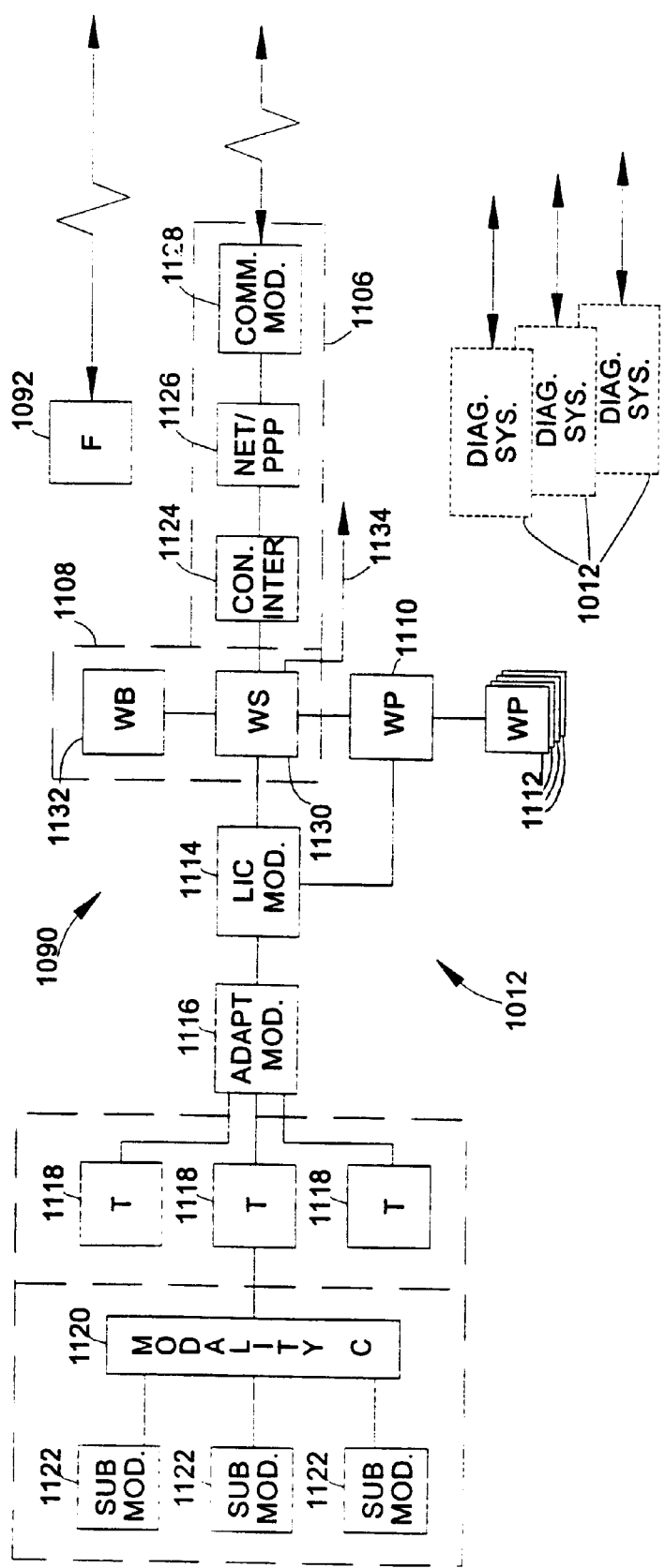
FIG. 6 is a block diagram of certain functional components within a diagnostic system of the type shown in FIG. 4 and FIG. 5 for facilitating interactive remote servicing of the diagnostic system.

FIG. 6 illustrates diagrammatically the various functional components comprising the uniform service platform 1090 within each diagnostic system 1012. As shown in FIG. 6, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanied with or without payment of a fee. Moreover, the particular arrangements managed by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 4 and 5).

In a present embodiment, the components comprising network connectivity module 1108 may be configured via an application stored as part of the uniform platform. In particular, a Java application licensed to a service engineer enables the engineer to configure the device connectivity at the diagnostic system to permit it to connect with the remote facility.

Figure 7:
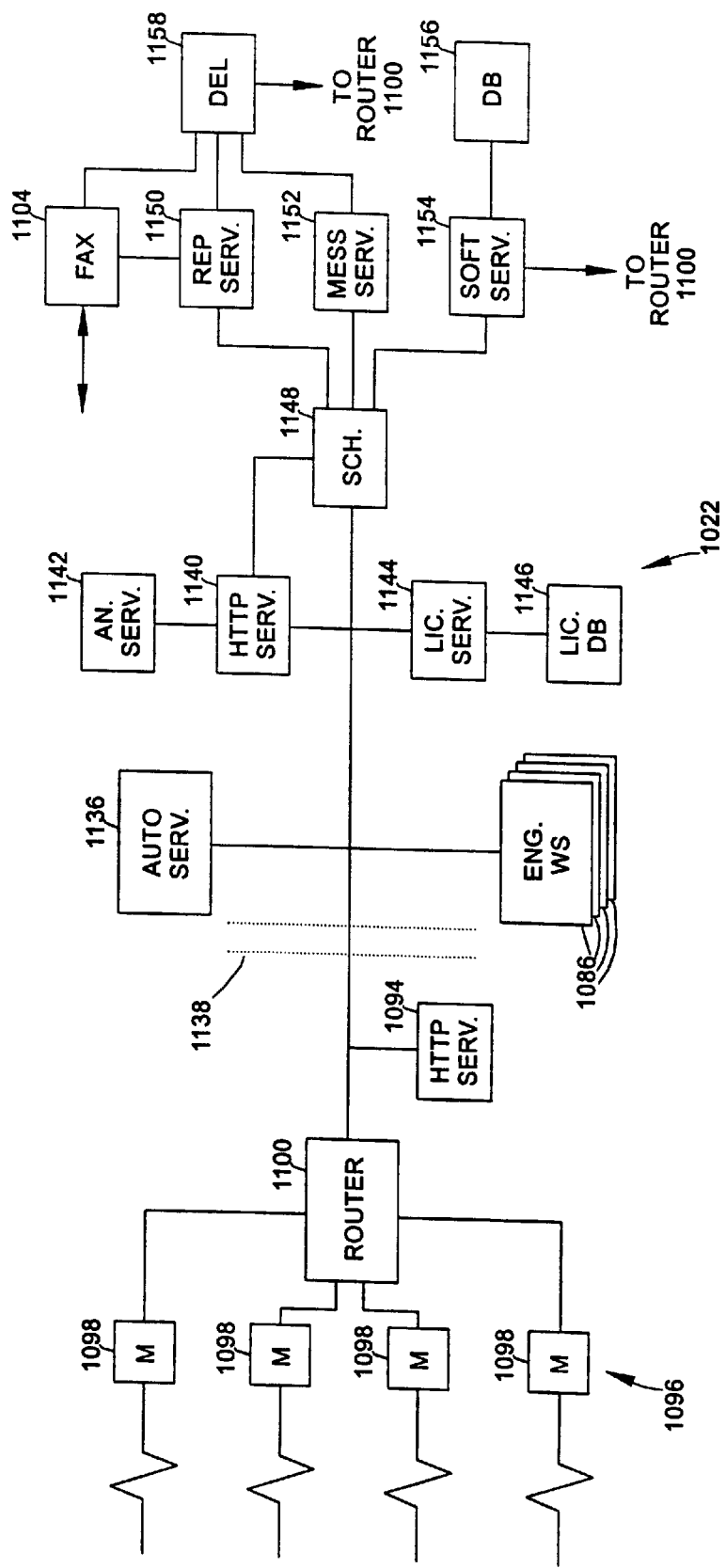
FIG. 7 is a block diagram of certain of the functional components of the remote facility illustrated in FIG. 4 and FIG. 5 for rendering interactive remote service to a plurality of medical diagnostic systems.

FIG. 7 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 7, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

Advantageously, where software upgrades are required for enhanced performance of a field replaceable unit or a non-replaceable unit, such software packages are sent directly to the diagnostic systems. As such, reconfigurations by FMI's or expensive field visits by technicians are avoided. Software upgrades can be offered by way of product tiers, new advancements, or changes in contract or license arrangements.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

The medical diagnostic systems described with reference to FIGS. 1–7 allow for factory information on a particular system component to be available for faster, more accurate installation (e.g., emission calibration data). Further, exemplary medical diagnostic systems can capture data on actual operation of an individual field replaceable unit or system unit, providing for warranty assessment, failure mode analysis, unit usage information from the site, usage trending, and the such. Examples of such unit operational data available includes system usage counter information, rotor on time, error log information, site installation information, and technique usage information.

While the embodiments illustrated in the FIGURES and described above are presently preferred, it should be understood that these embodiments are offered by way of example only. Other embodiments may include, for example, different types of information from the memory module or electronic device used with a particular medical diagnostic system. The invention is not limited to a particular embodiment but extends to various modifications, combinations, and permutations that nevertheless fall within the scope and spirit of the appended claims.

What is claimed is:

1. A method for configuring and monitoring a system unit in a medical diagnostic system, the method comprising:
   establishing a communication connection between the medical diagnostic system and a remote facility;
   communicating characteristic information regarding operation of the system unit in the medical diagnostic system from the remote facility to the medical diagnostic system;
   configuring the medical diagnostic system in accordance with the characteristic information regarding operation of the system unit; and
   monitoring the operation information of the system unit in the medical diagnostic system using an operator workstation at the medical diagnostic system.

2. The method of claim 1, wherein the step of configuring the medical diagnostic system is in accordance with characteristic information regarding operation of an x-ray tube, the x-ray tube being the system unit.

3. The method of claim 1, wherein the step of monitoring the operation information of system unit includes review by a service engineer.

4. The method of claim 1, further comprising the step of communicating the operation information to a remote operator workstation at the remote facility.

5. The method of claim 1, wherein the operation of the system unit is constrained to operation in accordance with a subscription file at the remote facility.

6. The method of claim 1, further comprising communicating the operation information of the system unit to an electronic device coupled to the system unit.

7. The method of claim 1, further comprising communicating new characterization information from the remote facility to the medical diagnostic system, the new characterization information providing for an adjustment in performance level of the system unit.

8. The method of claim 1, further comprising communicating identification information on the system unit from the medical diagnostic system to the remote facility, and verifying the identification information with a subscription file at the remote facility.

9. The method of claim 8, further comprising communicating new characterization information from the remote facility to the medical diagnostic system, the new characterization information being dependent upon changes in the subscription file associated with a particular system unit.

10. An apparatus which provides for the configuring and monitoring of a system unit in a-medical diagnostic system, the apparatus comprising:
    a storage medium coupled to the system unit which stores information for the system unit in the medical diagnostic system; and
    a communication interface configured to allow communications between the medical diagnostic system and a remote facility, the communications providing for the configuring of the medical diagnostic system to accept the system unit and for monitoring of the system unit.

11. The apparatus of claim 10, further comprising a programmed digital processing circuit coupled to the storage medium, the processing circuit being responsive to requests for information received from a remote facility via a network.

12. The apparatus of claim 11, wherein the apparatus comprises fasteners which couple the apparatus to an x-ray tube, the x-ray tube being the system unit.

13. The apparatus of claim 10, wherein the storage medium stores operation information related to operation of the system unit.

14. The apparatus of claim 10, wherein the storage medium stores characterization information related to operation of the system unit.

15. The apparatus of claim 14, wherein the characterization information comprises generic information to the system unit.

16. The apparatus of claim 14, wherein the characterization information comprises information specific to the system unit.

17. A system for configuring and monitoring a system unit in the medical diagnostic system, the system comprising:
    means for communicating characteristic information regarding operation of the system unit in the medical diagnostic system from the remote facility to the medical diagnostic system;
    means for configuring the medical diagnostic system in accordance with the characteristic information from the remote facility;
    means for communicating operation information of the system unit in the medical diagnostic system to the remote facility; and
    means for monitoring the operation information of the system unit in the medical diagnostic system.

18. The system of claim 17, further comprising means for verifying an identification of the system unit from the medical diagnostic system at the remote facility.

19. The system of claim 17, further comprising means for generating a service request from the medical diagnostic system to the remote facility.

20. The system of claim 17, wherein the means for configuring the medical diagnostic system is in accordance with characteristic information regarding operation of an x-ray tube, the x-ray tube being the system unit.

21. An x-ray tube comprising:

a vacuum vessel;

an anode assembly disposed in the vacuum vessel and including a target;

a cathode assembly disposed in the vacuum vessel at a distance from the anode assembly, the cathode assembly being configured to emit electrons which hit the target of the anode assembly and produce x-rays;

a programmed digital processing circuit; and an interface coupled to the processing circuit and at least the cathode assembly generating a signal representative of the cathode assembly and its operation, wherein the digital processing circuit is configured to manipulate digital data representative of the cathode assembly.

22. The x-ray tube of claim 21, wherein the processing circuit includes a communication circuit for communicating with a remote programmed digital processing circuit.

23. The x-ray tube of claim 22, wherein the remote programmed digital processing circuit is in an electronic device coupled to the x-ray tube.

24. The x-ray tube of claim 22, wherein the remote programmed digital processing circuit is located in a device separate from the x-ray tube.

25. The x-ray tube of claim 22, wherein the processing circuit is in a single package with the communication circuit and the interface.

* * * * *

UNITED STATES PATENT AND TRADEMARK OFFICE
CERTIFICATE OF CORRECTION

PATENT NO.    : 6,412,980 B1
DATED         : July 2, 2002
INVENTOR(S)   : Brian D. Lounsberry et al.

It is certified that error appears in the above-identified patent and that said Letters Patent is hereby corrected as shown below:

<u>Column 7,</u>
Line 28, after "in a" delete "ingle" and insert -- single --.

<u>Column 14,</u>
Line 23, after "in" delete "a-medical" and insert -- a medical --.

Signed and Sealed this

Eighteenth Day of February, 2003

JAMES E. ROGAN
*Director of the United States Patent and Trademark Office*